(12) United States Patent
Secrest et al.

(10) Patent No.: US 8,251,945 B2
(45) Date of Patent: Aug. 28, 2012

(54) ENDOSCOPIC SUCTION DEVICE

(75) Inventors: Dean J. Secrest, Concord, OH (US); Christopher J. Kaye, Concord, OH (US); Paul Davis, Carson City, NV (US); John P. Winstanley, Madison, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 1347 days.

(21) Appl. No.: 11/678,934

(22) Filed: Feb. 26, 2007

(65) Prior Publication Data

US 2007/0232859 A1 Oct. 4, 2007

Related U.S. Application Data

(60) Provisional application No. 60/776,247, filed on Feb. 24, 2006.

(51) Int. Cl.
*A61M 1/00* (2006.01)
*A61M 39/22* (2006.01)
*A61M 39/28* (2006.01)
*A61M 5/00* (2006.01)
*A61B 1/005* (2006.01)
*A61B 1/018* (2006.01)
*A61B 10/04* (2006.01)

(52) U.S. Cl. ......... 604/35; 600/159; 600/573; 600/576; 600/578; 600/579; 604/30; 604/34; 604/36; 604/48; 604/93.01; 604/245; 604/246; 604/247; 604/250; 604/256

(58) Field of Classification Search .......... 600/573, 600/575, 576, 578, 579, 159; 604/48, 93.01, 604/245, 246, 247, 250, 256, 30, 34, 35, 604/36
See application file for complete search history.

(56) References Cited

U.S. PATENT DOCUMENTS

| 1,937,362 | A | | 11/1933 | Schellberg |
| 2,701,559 | A | | 2/1955 | Cooper |
| 4,120,292 | A | | 10/1978 | LeBlanc, Jr. et al. |
| 4,198,958 | A | * | 4/1980 | Utsugi .......................... 600/154 |
| 4,263,516 | A | | 4/1981 | Papadakis |

(Continued)

FOREIGN PATENT DOCUMENTS

JP 11-267089 10/1999
(Continued)

OTHER PUBLICATIONS

International Search Report and Written Opinion from International Application No. PCT/US07/05086, dated Dec. 18, 2007.

(Continued)

*Primary Examiner* — Sean Dougherty
(74) *Attorney, Agent, or Firm* — Calfee, Halter & Griswold, LLP

(57) ABSTRACT

A device for suctioning material out of an instrument channel during an endoscopic procedure. The device includes a biopsy valve having a first end, a second end, and an outer circumferential surface. The biopsy valve defines an internal passage leading from the first end to the second end, wherein the first end is adapted for connection to an endoscope instrument channel inlet port. Tubing connects the biopsy valve second end to a suction source connector disposed remote from the biopsy valve. A flow controller is fixed to the tubing and disposed between the biopsy valve second end and the suction source connector. The device may include an irrigation port and an instrument entry port.

12 Claims, 4 Drawing Sheets

U.S. PATENT DOCUMENTS

| | | | | |
|---|---|---|---|---|
| 4,412,531 A * | | 11/1983 | Chikashige | 600/104 |
| D279,925 S | | 7/1985 | Wise | |
| 4,643,192 A | | 2/1987 | Fiddian-Green | |
| 4,736,732 A * | | 4/1988 | Shimonaka et al. | 600/158 |
| 4,842,580 A | | 6/1989 | Ouelette | |
| 4,944,729 A | | 7/1990 | Buckberg et al. | |
| 5,002,528 A | | 3/1991 | Palestrant | |
| 5,053,002 A | | 10/1991 | Barlow | |
| 5,078,688 A | | 1/1992 | Lobodzinski et al. | |
| 5,174,290 A | | 12/1992 | Fiddian-Green | |
| 5,186,172 A | | 2/1993 | Fiddian-Green | |
| 5,256,150 A | | 10/1993 | Quiachon et al. | |
| 5,269,781 A | | 12/1993 | Hewell, III | |
| 5,312,327 A * | | 5/1994 | Bales et al. | 604/21 |
| 5,312,400 A * | | 5/1994 | Bales et al. | 606/41 |
| 5,322,503 A * | | 6/1994 | Desai | 604/21 |
| 5,333,603 A * | | 8/1994 | Schuman | 600/108 |
| 5,336,174 A * | | 8/1994 | Daoud et al. | 604/30 |
| 5,336,220 A * | | 8/1994 | Ryan et al. | 604/22 |
| 5,395,349 A | | 3/1995 | Quiachon et al. | |
| 5,415,165 A | | 5/1995 | Fiddian-Green | |
| 5,429,596 A * | | 7/1995 | Arias et al. | 604/21 |
| 5,456,251 A | | 10/1995 | Fiddian-Green | |
| 5,474,450 A | | 12/1995 | Chronister | |
| 5,484,418 A | | 1/1996 | Quiachon et al. | |
| 5,653,697 A | | 8/1997 | Quiachon et al. | |
| 5,667,473 A * | | 9/1997 | Finn et al. | 600/104 |
| 5,674,193 A | | 10/1997 | Hayes | |
| 5,725,478 A * | | 3/1998 | Saad | 600/157 |
| 5,766,211 A | | 6/1998 | Wood et al. | |
| 5,800,493 A * | | 9/1998 | Stevens et al. | 607/113 |
| 5,935,122 A | | 8/1999 | Fourkas et al. | |
| 5,971,917 A * | | 10/1999 | Komi et al. | 600/159 |
| 6,010,453 A | | 1/2000 | Fiddian-Green | |
| 6,197,016 B1 | | 3/2001 | Fourkas et al. | |
| 6,413,228 B1 | | 7/2002 | Hung et al. | |
| 6,419,662 B1 | | 7/2002 | Solazzo | |
| D468,015 S | | 12/2002 | Horppu | |
| 6,626,827 B1 | | 9/2003 | Felix et al. | |
| 6,650,929 B1 | | 11/2003 | Nemoto et al. | |
| 6,699,184 B2 | | 3/2004 | Felix et al. | |
| 6,808,505 B2 | | 10/2004 | Kadan | |
| 6,808,521 B1 * | | 10/2004 | McMichael | 604/533 |
| 7,226,411 B2 * | | 6/2007 | Akiba | 600/154 |
| 2003/0069549 A1 * | | 4/2003 | MacMahon et al. | 604/266 |
| 2003/0176767 A1 * | | 9/2003 | Long et al. | 600/106 |
| 2004/0077938 A1 | | 4/2004 | Mark et al. | |
| 2005/0027165 A1 * | | 2/2005 | Rovegno | 600/154 |
| 2005/0113766 A1 | | 5/2005 | Mottola et al. | |
| 2005/0267417 A1 * | | 12/2005 | Secrest et al. | 604/247 |
| 2007/0043262 A1 * | | 2/2007 | Levy et al. | 600/156 |

FOREIGN PATENT DOCUMENTS

JP    2000-051144    2/2000

OTHER PUBLICATIONS

Office action from Japanese Application No. 2008-556480 dated May 18, 2012.

* cited by examiner

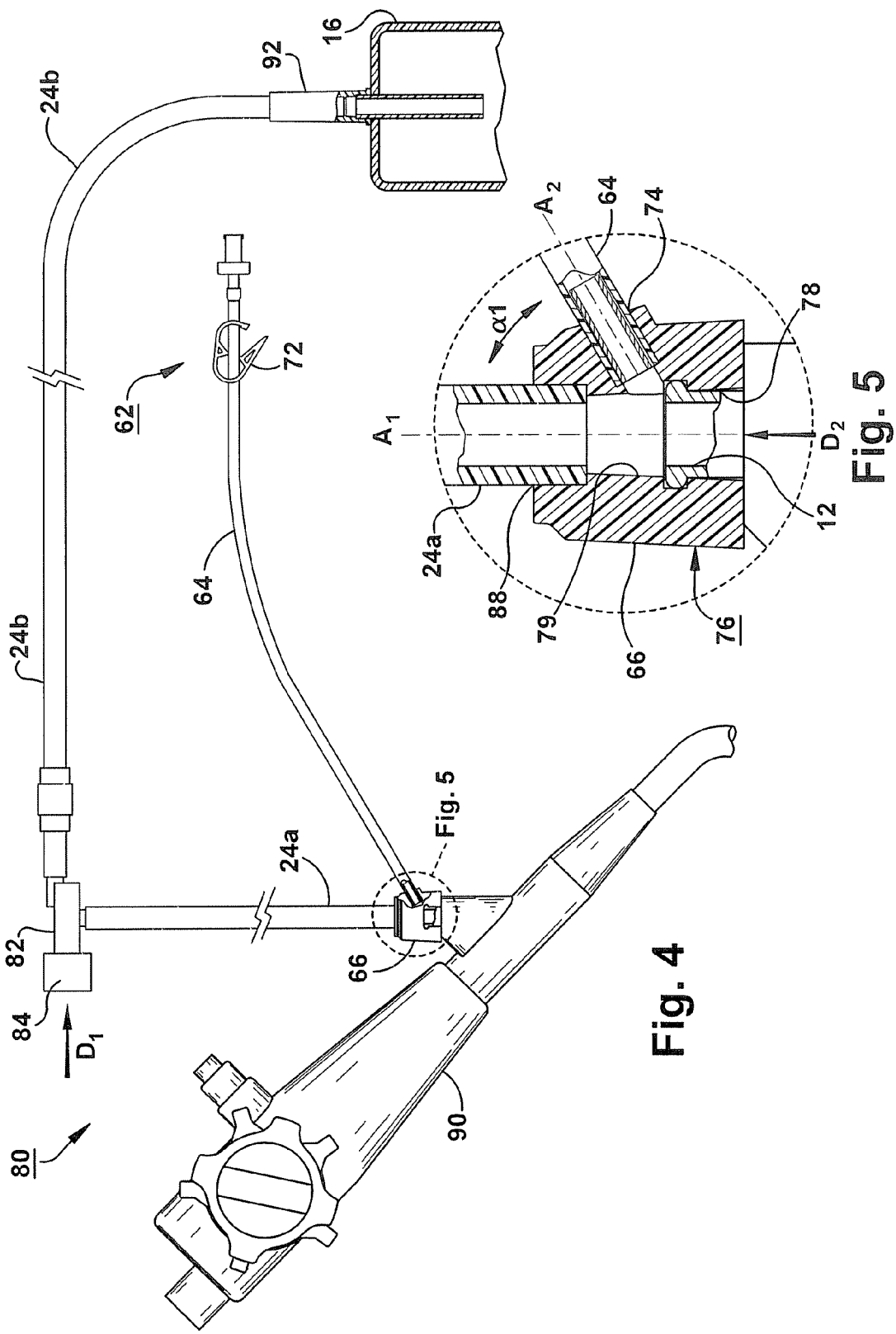

ENDOSCOPIC SUCTION DEVICE

CROSS-REFERENCE TO RELATED APPLICATIONS

This non-provisional application claims the benefit of U.S. Provisional Patent Application No. 60/776,247, entitled "Endoscopic Suction Device," filed Feb. 24, 2006, the entire disclosure of which is incorporated herein by reference, to the extent that it is not conflicting with this application.

FIELD OF THE INVENTION

The present invention relates to a suction device and to a suction device for use in removing fluid and material during an endoscopic procedure.

BACKGROUND OF THE INVENTION

Physicians perform endoscopic procedures within the gastrointestinal tract of a patient for a variety of different reasons. In an exemplary operation, an endoscope is inserted through a patient's esophagus and intubated to a work site. The endoscope is flexible and typically has optical and illuminating features that allow the physician to view the work site. Often during such procedures, it becomes necessary for the physician to evacuate blood clots or other materials in the gastrointestinal tract to clear the field of view. These materials are typically removed using components integral to the endoscope.

An endoscope typically has two trumpet valves located at the proximal end for the physician to control a suction line and an air/water line. Conventionally, an endoscopist would use the suction line to clear the blood clots. However, the suction line and/or the associated trumpet valve may clog if heavy or thick fluids are repetitively suctioned during a single procedure. Such clogging may require the procedure time to be extended by interruption of the procedure to clean the suction line, or in certain procedures, may require repeat intubation.

There remains a need in the art for a suction device that resists clogging, allows for repetitive suction of heavy or thick fluids during a single procedure, does not adversely extend procedure time, is easy to operate, and is inexpensive enough to warrant one-time use.

SUMMARY OF THE INVENTION

In several illustrated embodiments of the present invention, a suction device for evacuating blood clots or other materials from an endoscopic work site is disclosed. The suction device is designed for installation on the biopsy port of an endoscope. As such, the device is a direct suction device that does not rely upon the integral trumpet valves or suction line of the endoscope.

Further features and advantages of the invention will become apparent from the following detailed description made with reference to the accompanying drawings.

BRIEF DESCRIPTION OF THE DRAWINGS

FIG. 4 is a side plan view of yet another endoscopic suction device, showing a device having an alternative flow control valve;

FIG. 5 is an enlarged cross-sectional view of a designated portion of FIG. 4, showing structural detail of the biopsy valve connector installed on a biopsy port of an endoscope;

DETAILED DESCRIPTION OF THE INVENTION

This Detailed Description of the Invention merely describes embodiments of the invention and is not intended to limit the scope of the claims in any way. Indeed, the invention as described is broader than and unlimited by the preferred embodiments, and the terms used have their full ordinary meaning.

The present invention is designed for use by an endoscopist to clear blood clots, fluids, small tissue and other material from an internal work site adjacent the distal end of an endoscope. The device is a direct suction device that is designed for mounting between the biopsy port of an endoscope and a remote suction source. The biopsy port, also known in the art as the instrument channel inlet port, provides access to a biopsy inlet valve channel within the endoscope. Instruments may be inserted through this port for use at an internal work site. The biopsy port is located on the scope in an external point during a procedure, and distal relative to the endoscope trumpet valves with respect to the physician. The suction device utilizes the biopsy port channel, does not rely upon the integral trumpet valves and suction line of the endoscope.

Figure 1:
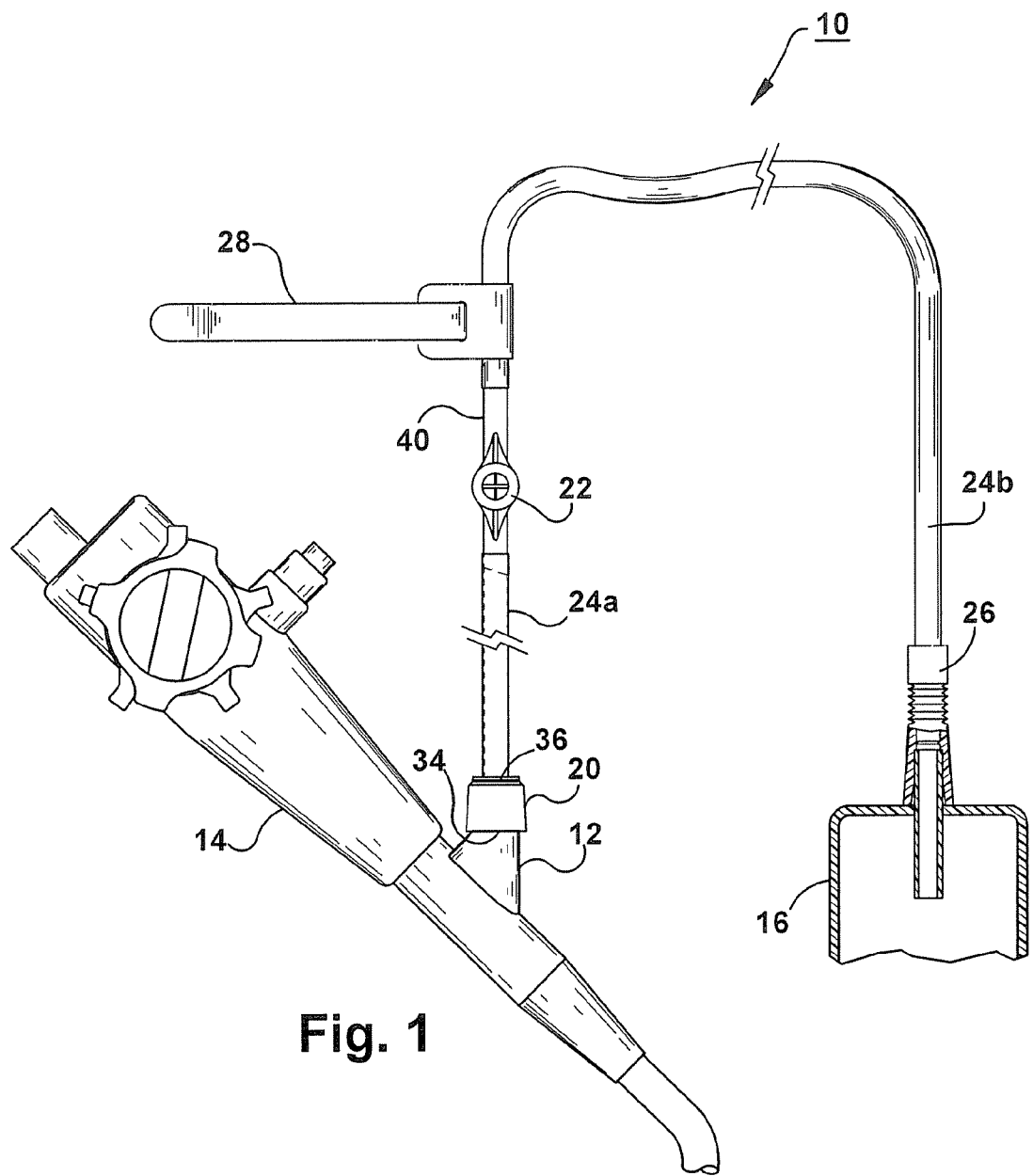
FIG. 1 is a side plan view of an endoscopic suction device attached between an endoscope biopsy port and a suction system, showing a device including a biopsy valve connector, a flow control valve, and a suction source connector.

Referring now to the drawings, FIG. 1 is a side plan view of a suction device 10 made in accordance with an embodiment of the invention. The device is illustrated installed onto the biopsy port 12 of an exemplary endoscope 14. A suction source 16 provides a suction to remove and collect materials pulled through the endoscope biopsy port channel and the device 10.

The device includes biopsy valve connector 20, a flow controller or control valve 22, tubing 24a, 24b and a suction source connector 26. As shown, the device also includes a strap 28 that an operator may use to steady the device against his or her finger, wrist or forearm. The strap may be physically attached to the device and helps maintain the position/orientation of the control valve to make operation easier. This feature also gives the operator a number of options. The operator can loop the strap on the index finger or thumb, maintaining proximate contact with the control valve until actuation is desired. Another option is to attach the device via the strap to the umbilicus of the endoscope so that the position of the turn valve is controlled and more readily accessible.

In an exemplary embodiment, the biopsy valve connector, or biopsy valve 20, is designed for quick installation on the biopsy port 12. The biopsy valve 20 may be constructed of flexible material to form an effective connection, such as for example, a press fit connection, on the biopsy port. The biopsy valve 20 includes a first end, or inlet port 34 and a second end, or outlet port 36. An internal passage (not shown in FIG. 1) is formed between the inlet port 34 and outlet port

36, having a longitudinal axis. Similar coaxial inlet and outlet ports 78, 88 about a longitudinal axis $A_1$ of an internal passage are shown in FIG. 5.

As discussed, a flexible piece of plastic tubing 24a connects the outlet port 36 and the control valve 22. The tubing 24a provides a fluid connection from the biopsy valve 20 to the control valve 22. The line 24a is constructed of flexible plastic tubing and provides a strain-relief/transition to the control valve 22. The length of the tubing 24a permits accessibility of the control valve remote from the endoscope. The length of tubing 24a between the biopsy valve 20 and the control valve 22 may be adequate to allow remote operation from the endoscope, such as for example, 12 inches. An additional suction line 24b leads from the downstream side of the control valve 22 to the suction source.

Still referring to FIG. 1, the control valve 22 is shown in an open position. The control valve 22 controls flow of materials through a main body 40. The control valve may be any suitable valve, such as for example, a simple turn valve or check valve. The main body 40 illustrated is a tube-shaped hard plastic molded base. The control valve 22 is less susceptible to clogging compared to an endoscope trumpet valve. As shown, opposing ends of the main body 50 are attached to the flexible tubing 24a, 24b. It should be apparent to others with ordinary skill in the art that various valve and main body designs can be utilized in the practice of the present invention. Further, various connection structure and techniques can be used between the main body 50 and the flexible tubing 24a, 24b. Also, any number of sections, combinations, sizes, or lengths of tubing may be used.

Figure 2:
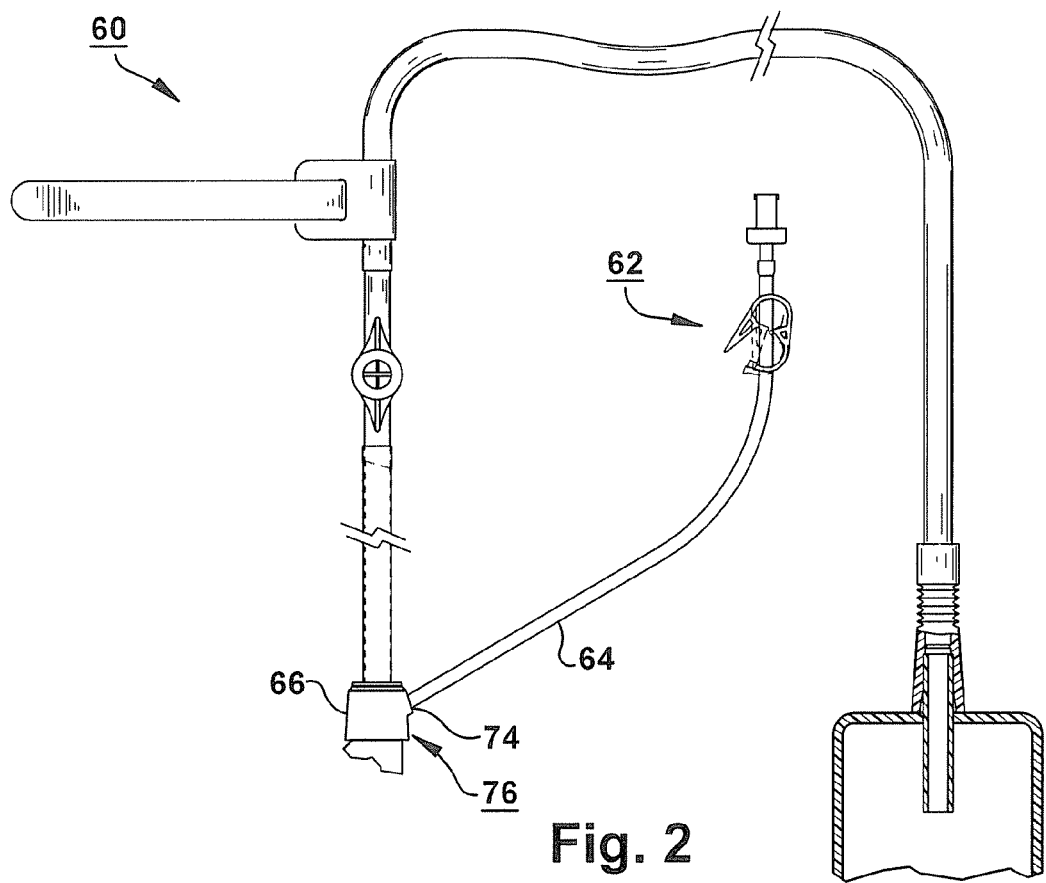
FIG. 2 is a side plan view of another endoscopic suction device, showing a device including an irrigation line.
Figure 3:
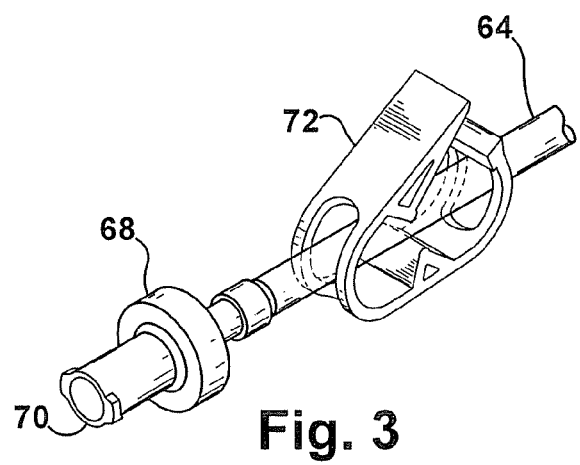
FIG. 3 is an enlarged perspective view of a flow control clamp shown on the irrigation line of FIG. 2.

Another exemplary embodiment of the invention is illustrated in FIG. 2. Often during evacuation procedures, the addition of water or other solvents are required to dilute materials or loosen blood clots. Conventionally, an endoscopist would use the air/water line of the endoscope to irrigate the work site for a more effective procedure. The device 60 shown in FIG. 2 includes an irrigation system 62 that advantageously does not utilize the air/water line of the endoscope. An enlarged perspective view of a portion of the irrigation system 62 is best shown in FIG. 3. The device 60 permits the delivery of fluid to the site during irrigation. Two exemplary methods for delivery include attaching either a syringe (typically 60 cc filled with saline) or an external pump (such as an ERBE™ brand). In either case, the delivery rate (pressure of the saline exiting the device) is minimal. A stand-alone pump that has greater delivery pressure could be utilized, but this is a relatively expensive option and the pressure would need to be limited or otherwise governed to ensure that no damage occurred to the mucosal wall. A hand or electric actuated pump apparatus that builds air pressure inside the saline reservoir (similar to a plant sprayer or other such device) could also be used. This device could be designed to deliver a maximum pressure that both helped to disrupt and clear the tissue site, without causing any collateral damage.

The irrigation system 62 includes a flexible plastic tube 64 connecting biopsy valve connector 66 and an injection luer 68. The tube 64 connects to a side entry port 74 in an outer circumferential surface 76 of the biopsy port 66. A needle can be inserted into the distal end 70 of the luer to inject solvents into the biopsy valve channel and subsequently to the internal work site. The luer may include a tethered cap. The cap has a two-fold purpose. First, it acts to isolate the outside environment from the internal fluids in the device to ensure no leaks occur. Secondly, it prevents air from being drawn through a clamp 72 into the system while the vacuum (suction) is being applied. The introduction of air would not necessarily be a functionally detrimental issue, but it does result in a whistling sound that can be a distraction/annoyance to the operator. The pinch clamp 72 can be used to prevent fluid travel in an opposing direction. The pinch clamp design may allow for one-hand operation. With the pinch clamp closed, fluids that are pulled under suction out of the biopsy port can not travel out of the injection luer 68.

FIG. 4 shows a side plan view of an endoscopic suction device 80 that includes an irrigation system 62, as discussed. The device also includes an alternative flow control valve 82. The control valve 82 is includes a button 84 pressable inward in a direction $D_1$ to maintain suction between the biopsy valve 66 and the suction source 16. Although the design may vary, an exemplary valve has a large lumen to facilitate suction and rotates freely from the open to close positions. To optimize a quick and effortless on/off turning operation, a push-button on/off device may be used, such as for example, a trumpet valve. A push-button actuated device that incorporates a spring to ensure the device is normally in the closed (no suction) position. Depressing the button creates an open flow path so that operation is initiated. Releasing downward pressure on the button allows the spring to drive the valve closed. This drastically improves the response time by eliminating delay between the on/off positions. In addition, partially depressing the button can result in a partially open channel, effectively limiting some of the suction pressure delivered to the site. It is believed that this ability to "feather" the amount of pressure provided can add to the operator's control.

FIG. 5 is an enlarged cross-sectional view of a designated portion of FIG. 4, and shows structural detail of the biopsy valve 66 installed on a biopsy port 12. As discussed, the biopsy valve 66, press fits over a standard endoscope stainless steel biopsy port 12. The valve 66 includes an inlet port 78, an outlet port 88 and a side entry port 74. As shown, the longitudinal axis $A_2$ of the side entry port is at an angle $\alpha_1$, as illustrated less than 90 degrees, from the longitudinal axis $A_1$ of the internal passage 79. This orientation allows injected fluid in the tube 64 to travel downward into the internal passage 79 and toward the biopsy port 12. As discussed, a flexible piece of plastic tubing 24a connects the outlet port 88 and the control valve 82.

The operation of the device 80 will now be discussed. Prior to the suction procedure beginning, the device 80 is installed on an exemplary endoscope 90 as shown in FIG. 4. The control valve 82 and the pinch clamp 72 should be closed. In other words, the button of the trumpet valve 82 should not be depressed. The end of the suction line 24b includes a suction connector 92 that attaches to a dedicated suction source 16. It should be noted that another connector design may be used, such as for example, a T-luer so that a shared suction source could be utilized. The control valve 82 is actuated to turn the device "ON" (engage suction) to generate suctioning power at the endoscope biopsy channel opening. By operation of the control valve 82 in this manner, flow of blood clots and other matter travels under suction out of the biopsy port in a direction $D_2$ and subsequently back through flexible tubing 24a, 24b to the suction source. When suction is no longer desired, either during or after the procedure, the control valve 82 is closed to turn the device "OFF" (static mode, no vacuum). As discussed, the device 80 is less susceptible to clogging than compared to an endoscope trumpet valve. Further, the device 80 is designed for one-time use and is believed to be economically disposable in intended applications.

When an endoscopist or team of technicians is performing an endoscopic procedure, it is often necessary to alternate uses of the biopsy port. In another exemplary embodiment of the invention, the biopsy valve structure supports the introduction of devices into the biopsy channel before, during, and after suctioning procedures. In certain conventional designs, the biopsy valve being utilized for the endoscopic procedure would need to be removed from the biopsy port prior to introduction of an instrument. After the instrument is installed and used as required, the instrument is removed prior to the biopsy valve being re-installed for designated device usage. If the instrument was again required, the procedure would be repeated.

Figure 6:
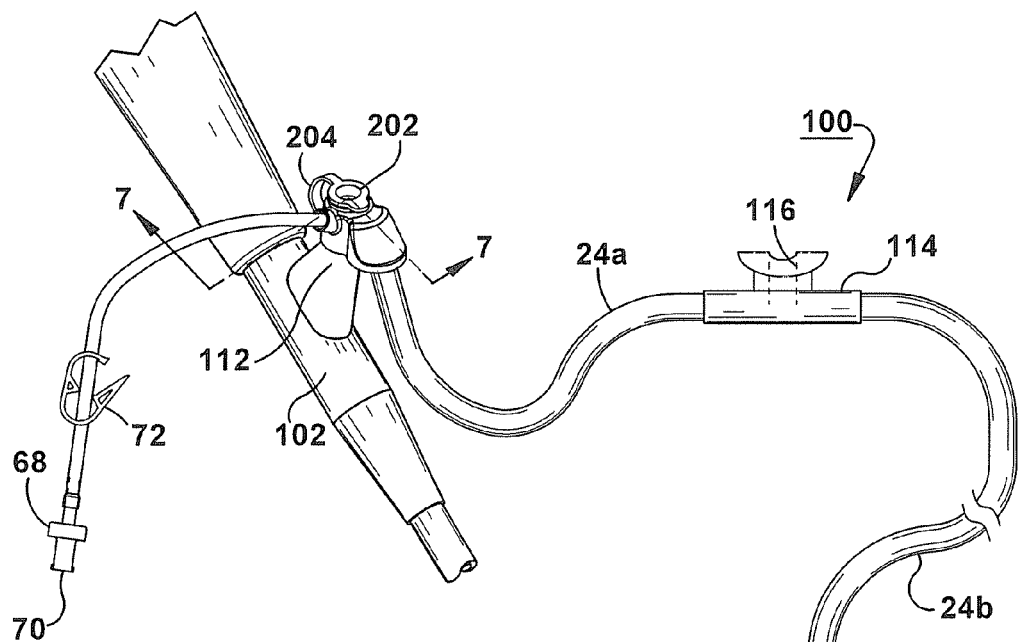
FIG. 6 is a perspective view of yet another endoscopic suction device, showing a device including an alternative biopsy valve connector and an alterative flow control valve.

FIG. 6 shows a perspective view an endoscopic suction device 100 attached to the biopsy port 112 of an exemplary endoscope 102. The device includes a biopsy valve 166, best shown in a cross-sectional view in FIG. 7, a control valve 114, suction tubing 24a, 24b, and a suction connector 116. The device provides a suction path between the biopsy port 112 and a direct suction source 16. The suction control is accomplished with a vented port controller 114 as shown in FIG. 6. The controller includes an open port 116 for finger operation, i.e., the port must be closed for suction to occur through the controller 114. It should be understood by others with ordinary skill in the art that several control valves have been discussed for purpose of example, and the invention can be practiced with any of these examples, or any other valve suitable in the art.

Figure 7:
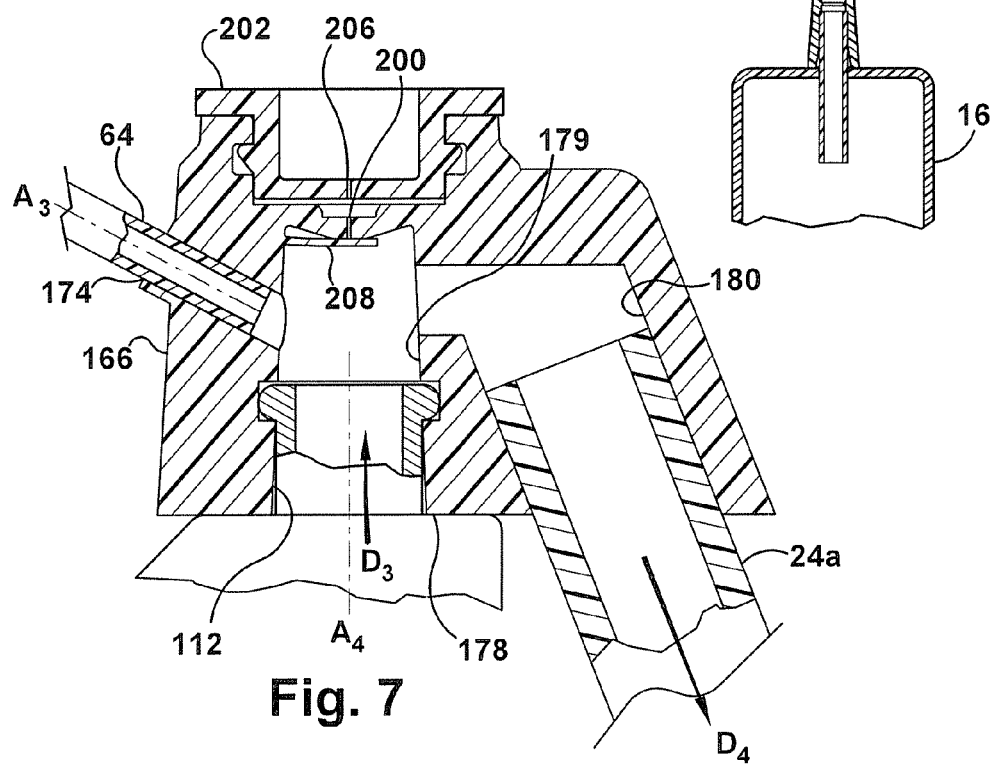
FIG. 7 is an enlarged cross-sectional view of the biopsy valve connector shown along the lines 7-7 of FIG. 6, showing structural detail of the biopsy valve connector installed on a biopsy port of an endoscope.

As discussed, the biopsy valve 166 shown in FIGS. 6 and 7 can remain installed on the biopsy port and with the two relevant access ports of the biopsy valve essentially intact so that irrigation and endoscopic instruments can be utilized as needed. In FIGS. 6 and 7, the biopsy valve 166 allows the attachment of the suction line 24a to be accomplished from below, allowing the irrigation line 64 to attach to a side entry port, and endoscopic instruments to enter the internal passage through an instrument entry port. Instruments that are inserted into the internal passage advantageously gain access to the instrument channel of the endoscope through the biopsy port.

Referring to FIG. 7, an enlarged cross-sectional view of the biopsy valve 166 is shown along the lines 7-7 of FIG. 6. As discussed, the biopsy valve 166, press fits over a standard endoscope stainless steel biopsy port 112. The valve 166 includes an inlet port 178, an outlet port 180, an instrument entry port 200 and a side entry port 174. An internal path 179 leads from the inlet port 178 to the outlet port 180. As discussed, a flexible piece of plastic tubing 24a connects the outlet port 180 and the control valve 114.

In this exemplary embodiment, the inlet port 178 defines an inlet travel path $D_3$ for suctioned material that is not co-linear with an exit travel path $D_4$ defined by the outlet port 180. As such, the tubing 24a does not extend directly out of the biopsy port, such as shown in FIGS. 1 and 4. It is believed that the exit orientation shown in FIGS. 6 and 7 is less distractive and more inconspicuous during the medical procedure.

Referring to the irrigation tubing orientation, the longitudinal axis $A_3$ of the side entry port is less than 90 degrees from the longitudinal axis $A_4$ of the inlet port 178. This orientation allows injected fluid to travel downward into the internal passage 179 and toward the biopsy port 112. It should be noted that the entry angle for the irrigation tubing can be equal to or greater than 90 degrees and still be effective. It has also been determined that the irrigation line could enter at another location (i.e. the tubing 24a) rather than in the valve body.

The instrument entry port 200 is a small aperture in the top of the biopsy valve 166. The entry port 200 is disposed opposite the inlet port 178 to provide direct axial access to the biopsy port. When inserting instrument of relatively small diameter, a cap 202 may be left in an installed position as shown. When inserting instruments of larger diameter, the cap may be removed. The cap is connected to the biopsy valve 166 by a tether 204 for convenience of use. As shown, the cap includes a center aperture 206 therethrough. The biopsy valve may include a flap member 208 internally mounted to the biopsy valve in the internal passage 179. The flap member inhibits fluid movement in a direction from the inlet port 178 of the biopsy valve to the instrument entry port 200. It should be understood that the cap and flap member disclosed are for exemplary purposes only, and that other structure can be utilized in the practice of the present invention to seal the instrument entry port during suction, including, but not limited to, sufficiently small diameter of the instrument entry port 200 in relation to the outlet port 180 of the biopsy valve 166.

The operation of the device 100 to perform suction is similar to the operation of the device 80 shown in FIGS. 4 and 5. Certain differences come in activities prior and after suction being performed. When an endoscopic procedure is required that will likely involve suctioning during the procedure, the device 100 is initially installed on the biopsy port 112 and the suction connector 116 is attached to the direct suction source. With the control valve 116, 82, 22 closed, the endoscopist can visually check the internal work site and determine if any suctioning is required. If so, the instrument entry port is closed, for example, by closing the cap 202, and the suction control valve is actuated until adequate suctioning has occurred, and the control valve is closed again. Without removing the biopsy valve 166, the required endoscopic instrument, such as for example, a snare, cutting, or injection device, can be inserted through the instrument entry port 200. As discussed, the size of the instrument will determine if the instrument is inserted with or without the cap removed. After the endoscopic instrument is removed, either during or after the procedure, the suctioning procedure can be repeated without removal of the biopsy valve 166.

While several embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the claims filed herewith.

What is claimed is:

1. A device for suctioning material during an endoscopic procedure, the device comprising:
   a) a biopsy valve having an inlet port, an outlet port, an instrument entry port, and an outer circumferential surface,
   b) tubing connecting said biopsy valve outlet port to a suction source connector disposed remote from said biopsy valve; and
   c) a flow controller fixed to said tubing and disposed between said biopsy valve outlet port and said suction source connector;
   d) wherein said biopsy valve defines an internal passage leading from said inlet port to said outlet port, said instrument entry port leads to said internal passage and wherein at least a portion of said inlet port is flexibly adapted to removably connect said biopsy valve to a biopsy port of an endoscope and to operatively connect said suction source connector to said biopsy valve to suction material from the endoscope.

2. The device of claim 1 wherein said biopsy valve outer circumferential surface defines a side entry port for injecting irrigation fluid through said biopsy port via said internal passage.

3. The device of claim 1 wherein said outer circumferential surface defines a side entry port, said side entry port defining a downward flow path toward said biopsy port angled less than 90 degrees from a longitudinal axis of said inlet port.

4. The device of claim 2 comprising an irrigation tube having an inlet end and an outlet end, said outlet end secured to said side entry port, wherein a fluid may be dispensed through said tube in a direction from said inlet end to said outlet end.

5. The device of claim 4 further comprising a controller disposed on said irrigation tubing to selectively prevent flow within said tube in a direction from said biopsy valve.

6. The device of claim 5 wherein said controller is a hand operated pinch clamp.

7. The device of claim 1 comprising a cap removably connectable to said instrument entry port for providing sealable access to said internal passage.

8. The device of claim 7 wherein said cap has a center aperture therethrough for providing access to said internal passage.

9. The device of claim 7 wherein said cap is securable to said biopsy valve in a spaced relation from said outer circumferential surface by a tether.

10. The device of claim 1 wherein said biopsy valve is constructed of a flexible plastic to form a press fit connection with said biopsy port.

11. The device of claim 1 comprising a flap member internally mounted to said biopsy valve in said internal passage, wherein said flap member inhibits fluid movement in a direction from said inlet port of said biopsy valve to said instrument entry port.

12. The device of claim 1 wherein said outlet port defines a suction exit path that is non-linear with a suction entry path defined by a longitudinal axis of said internal passage.

* * * * *